(12) United States Patent
Poland et al.

(10) Patent No.: US 6,217,516 B1
(45) Date of Patent: Apr. 17, 2001

(54) SYSTEM AND METHOD FOR CONFIGURING THE LOCUS OF FOCAL POINTS OF ULTRASOUND BEAMS

(75) Inventors: Mckee D Poland; George A Brock-Fisher, both of Andover, MA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/435,958

(22) Filed: Nov. 9, 1999

(51) Int. Cl.[7] .................................................. A61B 8/00
(52) U.S. Cl. ................................ 600/437; 600/447
(58) Field of Search .................................. 600/440, 443, 600/449, 438, 444, 445, 447; 73/625

(56) References Cited

U.S. PATENT DOCUMENTS

| 4,566,459 | * | 1/1986 | Umemura et al. .................. 600/437 |
| 4,938,217 | * | 7/1990 | Lele ................................. 600/437 |
| 5,379,642 | * | 1/1995 | Reckwerdt et al. ................. 73/625 |
| 5,471,989 | * | 12/1995 | Roundhi et al. .................. 600/443 |
| 5,533,510 | | 11/1996 | Koch, III et al. . |
| 5,577,505 | | 11/1996 | Brock-Fisher . |
| 5,879,303 | | 3/1999 | Averkiou et al. . |
| 5,967,985 | * | 10/1999 | Hayakawa ......................... 600/440 |

* cited by examiner

Primary Examiner—Marvin M. Lateef
Assistant Examiner—Maulin Patel

(57) ABSTRACT

The invention provides a method for controlling, in an ultrasound system, the loci of maximum power regions (e.g., focal points) of plural transmit lines of an ultrasound scan. Initially, a region being imaged is displayed and the user superimposes on the display a desired path to be traced by the loci of focal points of a scanned ultrasound beam. Data defining the path is then used to control an ultrasound transducer to produce a sequence of ultrasound beams that scan the region and to adjust the foci of the individual ultrasound beams so that they track the desired path. It is preferred that a graphical input device be used to trace the path of the loci on the display. The invention further enables data derived from the selected loci of maximum power regions to enable adjustment of both power and focal depth of the respective beams.

22 Claims, 4 Drawing Sheets

FRAME TABLE

| LINE # | ANGLE | FOCAL DEPTH | OTHER COEFFICIENTS |
|---|---|---|---|
| 1 | −45 | 9cm | ... |
| 2 | −44.5 | 9cm | ... |
| 3 | −44 | 9cm | ... |
| ... | ... | ... | ... |
| 10 | −40.5 | 9cm | ... |
| 11 | −40 | 7.5cm | ... |
| 12 | −39.5 | 7.5cm | ... |
| ... | ... | ... | ... |
| 27 | −33 | 7.5cm | ... |
| 28 | −32.5 | 4cm | ... |
| 29 | −32 | 4cm | ... |
| ... | ... | ... | ... |
| Etc. | | | |

FIG.3

TRANSMIT FOCUS COEFFICIENTS

| LINE 1 CHANNELS | TRANSMIT DELAYS | | | | | | | |
|---|---|---|---|---|---|---|---|---|
| 000−007 | 400 | 403 | 406 | 409 | 412 | 415 | 417 | 420 |
| 008−015 | 423 | 426 | 428 | 431 | 433 | 436 | 438 | 441 |
| 016−023 | 443 | 445 | 448 | 450 | 452 | 454 | 451 | 453 |
| 024−031 | 455 | 457 | 459 | 461 | 463 | 464 | 466 | 468 |
| 032−039 | 469 | 471 | 472 | 474 | 475 | 476 | 478 | 479 |
| 040−047 | 480 | 481 | 482 | 483 | 484 | 485 | 486 | 487 |
| 048−055 | 488 | 489 | 489 | 490 | 491 | 491 | 492 | 492 |
| 056−063 | 492 | 493 | 493 | 493 | 494 | 494 | 494 | 494 |
| 064−071 | 494 | 494 | 494 | 494 | 493 | 493 | 493 | 492 |
| 072−079 | 492 | 492 | 491 | 491 | 490 | 489 | 489 | 488 |
| 080−087 | 487 | 486 | 485 | 484 | 483 | 482 | 481 | 480 |
| 088−095 | 479 | 478 | 476 | 475 | 474 | 472 | 471 | 469 |
| 096−103 | 468 | 466 | 464 | 463 | 461 | 459 | 457 | 455 |
| 104−111 | 453 | 451 | 454 | 452 | 450 | 448 | 445 | 443 |
| 112−119 | 441 | 438 | 436 | 433 | 431 | 428 | 426 | 423 |
| 120−127 | 420 | 417 | 415 | 412 | 409 | 406 | 403 | 400 |

FIG.4

SYSTEM AND METHOD FOR CONFIGURING THE LOCUS OF FOCAL POINTS OF ULTRASOUND BEAMS

FIELD OF THE INVENTION

This invention relates to ultrasound imaging systems and, more particularly, to a method and apparatus for enabling the user to modify and configure the locus of ultrasound beam focal points during a scan action.

BACKGROUND OF THE INVENTION

The use of linear and two-dimensional phased arrays of ultrasound transducers to achieve focus ultrasound beams is well known in the prior art. Such transducers employ a plurality of ultrasound-generating elements which are controlled to provide the ultrasound beam with a determined focal points. Such is achieved by control of the time of firing of the respective transducer elements. The scan of the ultrasound beam is accomplished by pulsing the ultrasound elements at different relative times to produce each beam (or "line"). Accordingly, as the relative timing of the energizations of the respective transducer elements changes, the azimuth taken by the beam moves in the direction of the scan.

Since the focusing of the ultrasound beam occurs through the control of the time of firing of the respective elements, the focus is predetermined at the time of firing of the elements. It is a characteristic of an ultrasound beam, at its focus, that a maximum level of ultrasound pressure is present. This feature is important when a contrast agent is utilized during the ultrasound imaging action.

The most widely used contrast agent comprises microbubbles that produce a strong nonlinear response when illuminated by an ultrasound beam. If the ultrasound beam exhibits, at its focus, an acoustic pressure which exceeds a threshold value, the contrast agent microbubbles can be burst. Use of this phenomenon during flow imaging enables a user to determine the time required to re-perfuse a flow region after the contrast agent therein has been destroyed by a high pressure ultrasound beam.

In current ultrasound systems, only one transmit focus is typically present per acoustic line or beam. To achieve the benefits of multiple transmit foci along a single scan direction, the prior art has used a "splice mode" wherein multiple acoustic lines are generated along the same azimuth, but with different focal depths as a result of altered timing of energizing pulses to the transducer elements. Data from the multiple co-linear acoustic lines are then combined to form a single composite image line with multiple foci. Other than the splice mode, a sector scan format used by current ultrasound systems produces focus loci which are semicircles that are centered at the apex of the scan.

The concentration of acoustic power at the focal point of an ultrasound beam provides a number of benefits. The echo signal-to-noise ratio in a region of interest is generally greater in echo signals received from the beam's focal point. Greater destruction of a contrast agent is achievable at the beam's focal point. This is especially useful in harmonic imaging methods that include subtraction of pre and post destruction image data.

As stated above, current ultrasound systems exhibit loci of focal points that are positioned along fixed, regular curves, e.g., in a sector scan, the locus of all beam foci are along a semicircle. There are, however, many anatomical features that present irregular outlines which are not aligned with the regular loci of focal points found in current ultrasound systems. For instance, when imaging cardiac walls, it would be desirable to control the loci of the ultrasound beam focal points to track the cardiac walls so as to achieve improved imaging thereof, or when contrast agent is being used, to enable improved its imaging or destruction.

Accordingly, due to the variability of anatomical structures, it would be useful to enable the user to define a path over which beam foci would track so as to enable an improved imaging of irregular anatomical structures.

SUMMARY OF THE INVENTION

The invention provides a method for controlling, in an ultrasound system, the loci of maximum power regions (e.g., focal points) of plural transmit lines of an ultrasound scan. Initially, a region being imaged is displayed and the user superimposes on the display a desired path to be traced by the loci of focal points of a scanned ultrasound beam. Data defining the path is then used to control an ultrasound transducer to produce a sequence of ultrasound beams that scan the region and to adjust the foci of the individual ultrasound beams so that they track the desired path. It is preferred that a graphical input device be used to trace the path of the loci on the display. The invention further enables data derived from the selected loci of maximum power regions to enable adjustment of both power and focal depth of the respective beams.

BRIEF DESCRIPTION OF THE DRAWINGS

FIG. 3 illustrates a frame table that includes the angle and quantized focal depth entries for each imaging line, according to a mapped power locus path.

FIG. 4 illustrates a table of transmit delays of pulses applied to an element of a phased array transducer. The exemplary transducer is assumed to have 128 ultrasound elements.

DETAILED DESCRIPTION OF THE PREFERRED EMBODIMENT

Figure 1:
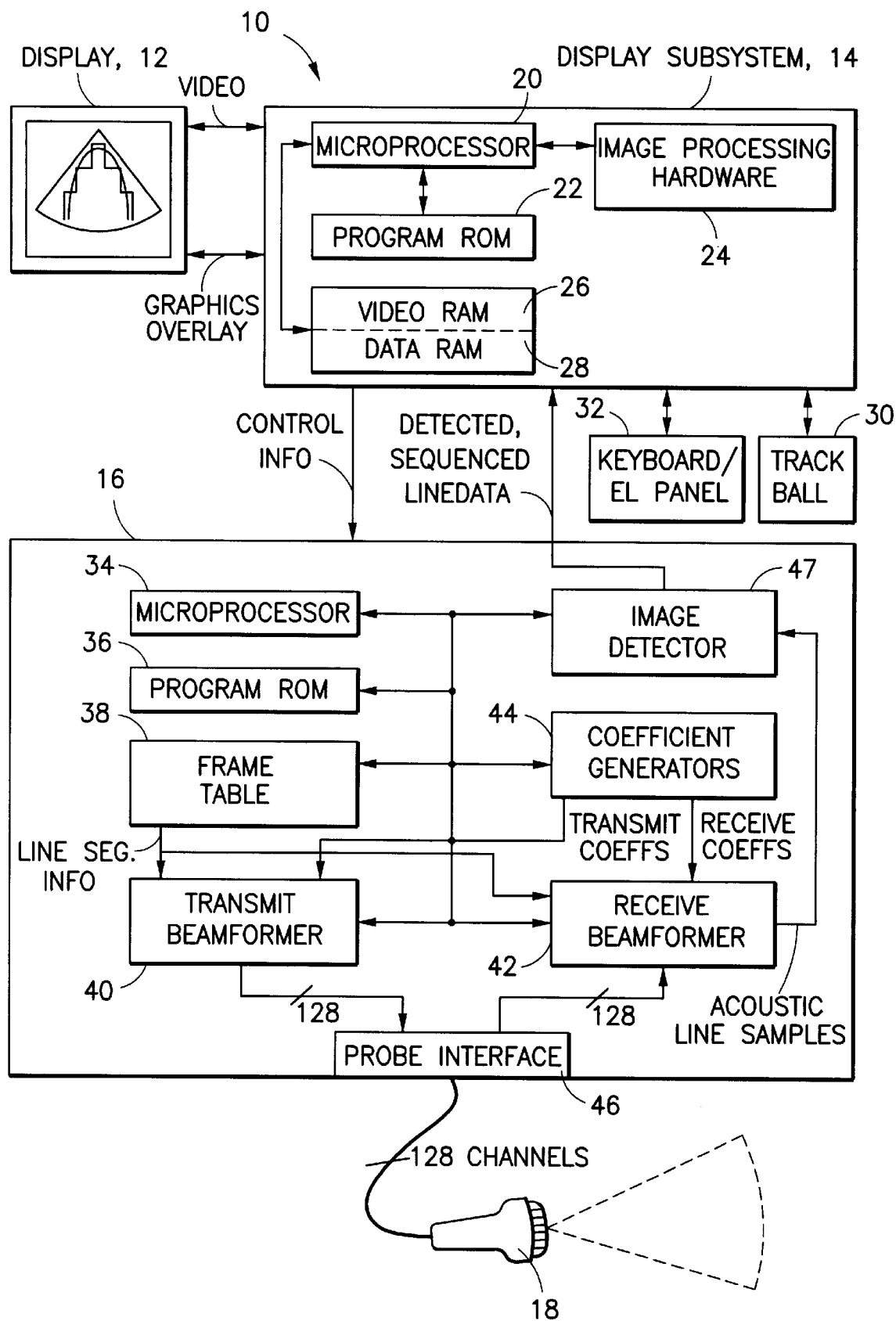
FIG. 1 is a system block diagram of an ultrasound system that is adapted to implement the invention.

Referring to FIG. 1, ultrasound system 10 comprises four main units, display monitor 12, display subsystem 14, scanner subsystem 16, and acoustic transducer 18. Display subsystem 14 includes a microprocessor 20 and a program read-only memory (ROM) 22 which, together with image processing hardware 24, controls the operation of display monitor 12. Video and data random access memories 26 and 28 store, respectively, video data that is to be presented on display monitor 12 and data which is used by microprocessor 20 and image processing hardware 24 during the processing of the video data.

A trackball 30 serves as a graphical input device for display subsystem 14 and enables graphical images to be formed on the face of display monitor 12. The position of such a graphical image on display monitor 12 is determined and operated upon by display subsystem 14. A keyboard 32 provides an alternative user input for display subsystem 14.

Scanner subsystem 16 is controlled by a microprocessor 34 in conjunction with data stored in program ROM 36. A frame table 38 includes control data that is used to control the operations of transmit beam former 40 and receive beam former 42. A coefficient generator 44 is coupled to both transmit beam former 40 and receive beam former 42 and outputs coefficients that control the timing of actuation of the acoustic elements that comprise transducer 18.

Briefly stated, transmit beam former 40, based on the input data from frame table 38 and coefficient generator 44, outputs transmit pulses via a probe interface 46 to each of the acoustic elements that comprise transducer 18. In accordance with the timing of pulses applied to the acoustic elements, the beam emanating from transducer 18 will be caused to translate in a manner which forms a scan, such as by displacing each successive beam by a given distance or angle in space. Further, the timing of such pulses (and their magnitudes) control the focal points and beam powers that are generated by acoustic transducer 18. Received echo signals are fed to receive beamformer 42 which, in turn, feeds acoustic line samples to image detector 47. The outputs from image detector 47 comprise detected, sequenced line data that are transmitted to display subsystem for further processing and display.

Insofar as the overall operation of ultrasound system 10 is concerned, it is generally conventional and in conformance with the prior art. However, the operation of ultrasound system 10 departs from the prior art in that scanner subsystem 16, in response to inputs from trackball 30 (or some other graphical input device) is enabled to alter the energization of the acoustic elements in ultrasound transducer 18 in such a manner as to cause the foci of the plural output beams to track a path that is input by the user, rather than to traverse a fixed, invariable path. In such manner, the image presentation appearing on display monitor 12 is improved. The improvement results from the locus of the foci of the beams following an anatomical structure, rather than taking a fixed scan path.

Figure 2:
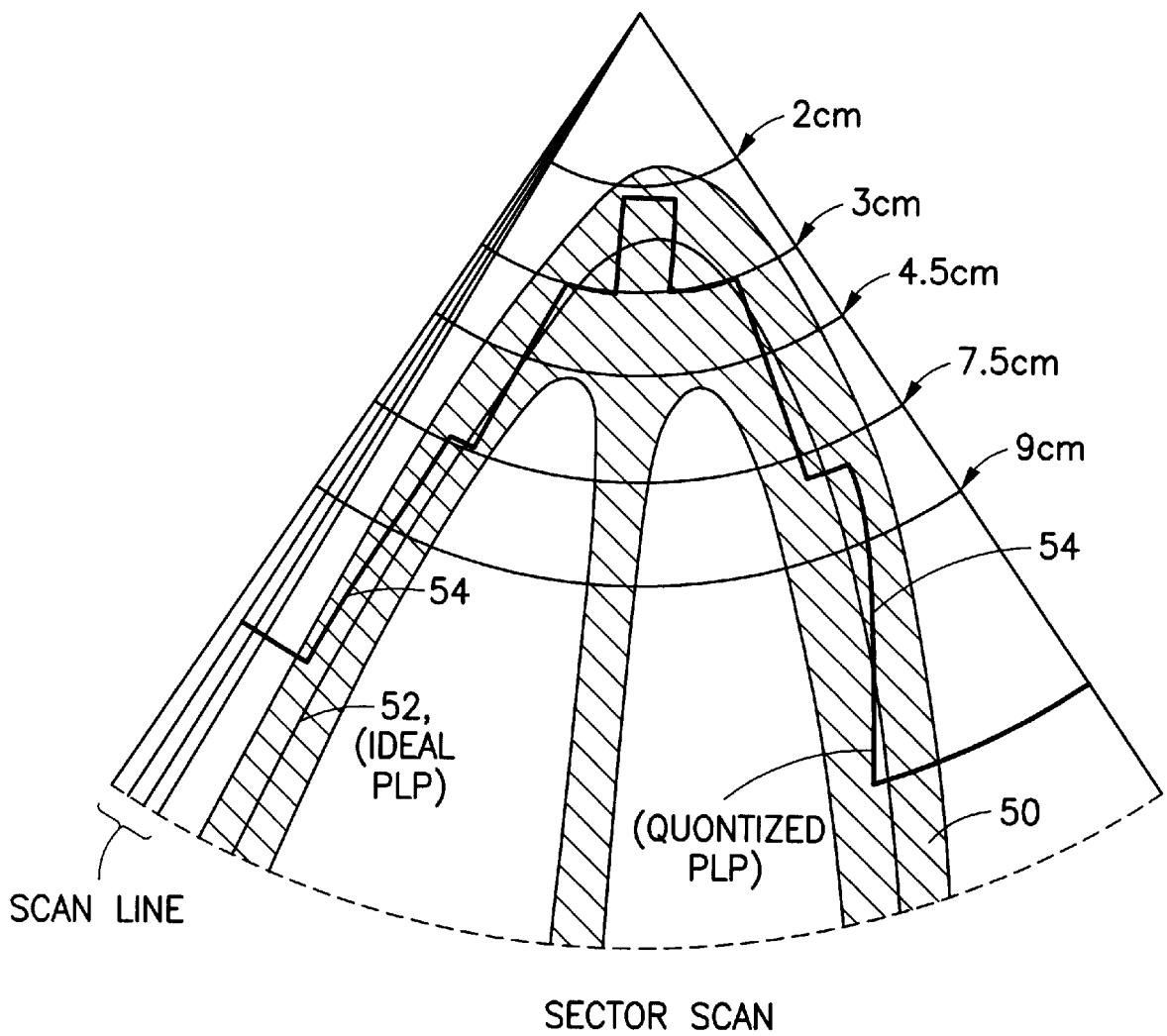
FIG. 2 illustrates a sector scan of an apical view of cardiac walls, illustrating a power locus profile superimposed thereon.

In the preferred embodiment of the invention, a user draws an ideal, desired power locus profile (hereafter "ideal PLP") on display monitor 12 over an existing ultrasound anatomical image, such as the sector scan image shown on display monitor 12 and its expanded version shown in FIG. 2. The image may be live (from continuous scanning) or frozen (such as with triggered scanning, or as a result of activating the "freeze" control). Image 50 shown in FIG. 2 is an apical view of the cardiac walls. Image 50 is generated by a combination of software and hardware and through use of standard ultrasound imaging procedures. The software portion resides in program ROM 22 in display subsystem 14, and executes on microprocessor 20. The input image data to display subsystem 14 is detected, sequenced, line data from the Scanner subsystem 16. The standard ultrasound image processing methods for sector scan formats are well understood and documented elsewhere.

The user draws a line on display monitor 12 by touching a key on keyboard 32 to enter a "PLP Draw" mode. In response, a cursor shown on the display changes to indicate the draw mode is active. The user then moves the system trackball to move the cursor, which draws a line 52 on the display as a pixel trail. Line 52 preferably tracks the region of the displayed anatomical image (i.e., cardiac wall 50 whose presentation is to be enhanced. A standard line erasing/editing facility allows the user to redraw or correct the ideal PLP.

The ideal PLP is stored, pixel-by-pixel, as a graphics overlay to the ultrasound image in video RAM 26 of display subsystem 14. When the user has finished drawing the ideal PLP, the user touches another key on keyboard 32 to confirm the entry, and the system responds by calculating and displaying a quantized PLP 54. Alternatively, display subsystem 14 can calculate and update a portion of quantized PLP 54 as the user is drawing, allowing the user to back up and make quick corrections more readily.

Quantized PLP 54 is a piecewise linear approximation to ideal PLP drawn by the user and manifests system constraints on the PLP. The primary constraint is a quantization of focus for every individual scan line. The PLP can only occupy a distinct set of transmit foci available in the system. Although transmit coefficients for any focus depth can be generated algorithmically, only a practical subset of foci are characterized for transmit power, subject to FDA limits. Therefore, the choice of focus for any scan line must be taken from an available set of pre-determined foci $F_j$ for the particular probe and scan format, where j is the index of available foci.

FIG. 2 shows, as an example, 6 discrete foci. They range from 2 to 12 cm. In the example shown in FIG. 2, actual PLP 52 must intersect only one focus for any scan line. (Representative scan lines 56 are shown to the left of FIG. 2). The curved portions of actual PLP 52 represent groups of scan lines that have the same focal depth F.

In forming the graphical representation of actual PLP 52 as visual feedback to the user, the straight radial segments of quantized PLP 54 each coincide with a single scan line 56, and represent the boundaries between groups of lines that share the same discrete focus. The radial segments of actual PLP 52 are thus construction elements of the locus only which allow the user to better see the path of the locus.

Quantized locus 54 is found by taking user-drawn ideal PLP 52 from the graphics overlay in video RAM 26 and converting it from a set of X–Y points (i.e., Cartesian coordinates) to a radial format (i.e., a set of points in polar coordinates r, q). Ideal PLP 52 in r, q coordinates is mapped to the nearest focus $F_j$ for each scan line angle $q_i$, where i is the index of scan lines 56. For each point r, q in ideal PLP 52, the nearest $q_i$ is found first by searching, and then the nearest $F_j$. The mapping can be done either in display subsystem 14 or in scanner subsystem 16, under control of one of the subsystem programs stored in the subsystem's program ROM and executed on the subsystem's microprocessor.

The result of the mapping is a Frame Table, an example of which is shown in FIG. 3. The Frame Table is indexed by scan line number i, and includes the angle and quantized focal depth entries for each line according to mapped ideal PLP 52. The Frame Table also typically contains many other data fields in each line entry for control of other aspects of the scan generation, such as image processing parameters (e.g. B-Mode, Color Flow, PW Doppler). Frame Table entries may also contain other coefficients that affect power locus (as described below). The Frame Table is stored in RAM in the scanner subsystem 16 and is used in the scanning process to control acquisition of acoustic data.

Once the focal depth for each scan line is known, transmit coefficients are generated in scanner subsystem 16 under control of microprocessor 34 and program ROM 36. Coefficient generators 44 for both transmit and receive coefficients supply data to transmit and receive beamformers 40 and 42, respectively. For both transmit and receive, a primary function of the coefficients is to control focus, steering, amplification and apodization of the acoustic beams. For transmit beamformer 40, the coefficients may also determine the following parameters of the transmit waveforms, element-by-element:

pulse burst length (number of cycles), pulse burst amplitude envelope shape, pulse amplitude (peak-to-peak transmit voltage in a burst), center frequency, spectral bandwidth, and aperture (which elements, in what pattern are active).

For the purposes of this example, only the path of the transmit focus across the scan lines is used as the determinant of power locus. For each scan line i, a set of transmit delays is calculated by Coefficient Generators 44 for the elements of probe 18's phased array. The transmit burst from each probe element is timed by this set of delays in order to create the desired steering angle $q_i$ and focus $F_i$ for the line i.

FIG. 4 shows a table of transmit delays for 128 system channels. (Probe 18 may have greater or fewer elements than 128), Each channel is connected through probe interface 46 to an element of phased array probe 18. The distance between elements on the probe face is accounted for in calculating the transmit coefficients for the scan.

During scanning, microprocessor 34 in scanner subsystem 16 steps through each line number i in sequence. For each scan line, control information is sent from the Frame Table to the beamformers, causing the pre-calculazed transmit and receive coefficients to be activated and used in beamforming. In transmit beamformer 40, the coefficients will have been modified to use quantized PLP 52. Accordingly, the coefficients for each scan line enable the acoustic elements to adjust the focus of the ultrasound beam so that succeeding beam foci follow the route of quantized PLP 54.

Figure 5:
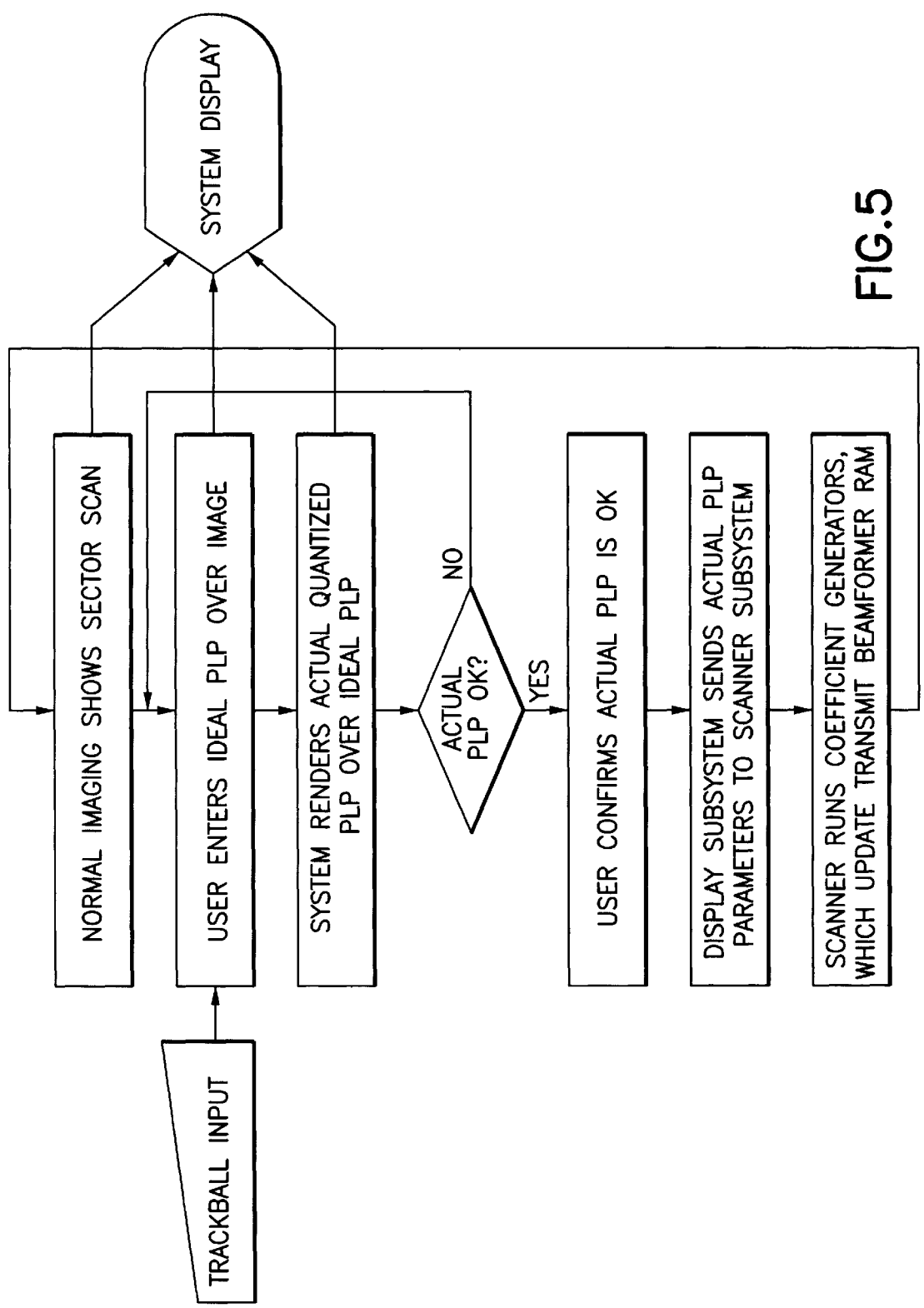
FIG. 5 is a logic flow diagram which illustrates the method for creation and use of a power locus profile.

A logic flow diagram for the process of creating and using the PLP is summarized in FIG. 5. Note that the user is enabled to alter ideal PLP 52 until it is set to follow the path of the anatomical image along which enhanced images are desired.

The control of transmit parameters for locating the path of maximum acoustic power in the medium has been described above.

"Multi-burst" techniques employ more than one transmit event per scan line and have been shown to enhance the detection of non-linear acoustic media, especially in the presence of contrast agents. An example is cited in U.S. Pat. No. 5,577,505, wherein transmit power modulation from line to line allows suppression of linear signal response and amplification of non-linear response. Use of a power locus profile in a region of interest will complement and augment power modulation and similar multi-burst techniques.

Splicing techniques are well known in ultrasound imaging and enable two or more transmit events to be emitted in the same direction but with different focal depths. The received data from both events are combined by splicing the sections of the receive lines that are close to the corresponding transmit line's focus. The result is a single, composite receive line that benefits from narrower average focus over the whole line depth. Using a splice technique, the PLP can be extended such that its path may cross radial scan lines at more than one point, because for a given scan line, multiple foci from multiple transmit events may be spliced together.

The embodiment discussed above uses a radial scan line pattern as its basis. Scan line patterns other than sector scans are in common use, including rectangular and trapezoidal. Those patterns require only changes to the coefficient generation formulae for determining element by element delay, for a given focal depth. Thus a PLP, as described above, can be used to set the pattern of focal depths in such scan patterns. In the focus generation step, the mapping of ideal to actual PLP must use the coordinates of the actual scan lines in a coordinate system most suited to the scan format. For instance, Cartesian coordinates are best suited to rectangular shaped scans.

The invention is not only useful for contrast imaging, but is useful in any ultrasound scanning of non-linear media, including body tissues. Because the non-linear effect is most pronounced where acoustic power is most concentrated, it is desirable to allow control over the locus of maximum power. For instance, in "tissue harmonic" imaging, PLP will aid in image enhancement because harmonic echoes (from non-linearity in tissues) are exploited to enhance the image contrast and to reduce clutter.

The embodiment described above relates to 2-dimensional ultrasound scanning, where the acoustic beams formed by the scan lines are all coplanar. (The acoustic lines each have an elevation focus profile, but the scanner does not vary it.) That limitation is unnecessary in that the PLP can occupy 3-dimensional space. Standard 3-D rendering equipment can allow the user to construct a 3-D ideal PLP. The locus of transmit foci can be varied in 3 dimensions, using a 2-dimensional phased array probe. In a 3-D scanning system, each scan line interrogates the surrounding volume, which can optimally be a frustum if the scan lines have a common apex. In that scanning configuration, the focus of each scan frustum is determined by a mapped 3-D PLP. Again, transmit parameters other than just focus can be applied to each frustum.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for controlling, in an ultrasound system, a locus of maximum power regions of plural beam transmit lines of an ultrasound scan, said method comprising the steps of:

a) producing a display of an imaged region;

b) superimposing on said display of said region, indications of a desired locus of maximum power regions of said plural beam transmit lines of said ultrasound scan; and c) controlling an ultrasound transducer to (i) produce ultrasound beams that scan said region, and (ii) adjust said beams so that maximum power regions thereof occur, during said ultrasound scan, in accord with said indications.

2. The method as recited in claim 1, wherein step c) produces each said maximum power region of a beam by adjusting a focal point thereof.

3. The method as recited in claim 1, wherein said indications are configured as a graphical image on said display.

4. The method as recited in claim 1, wherein step (b) enables a user to superimpose said indications on said display and further enables said user to adjust said indications so as to revise their position on said display in relation to an anatomical construct imaged on said display.

5. The method as recited in claim 2, wherein said controlling step (c) maps said indications to respective closest allowed focal points, which allowed focal points are in turn used to control said focus of said ultrasound beam.

6. The method as recited in claim 5, wherein each said ultrasound scan comprises N transmit events of an ultrasound beam, plural ones of said transmit events controlled to manifest foci in accord with said closest allowed focal points.

7. The method as recited in claim 2, wherein the locus of foci is adjusted during controlling step (c) by adjusting coefficients used to control a transmit beam former forming a portion of said ultrasound system.

8. The method as recited in claim 1, wherein said controlling step (c) employs data derived from selected loci of maximum power regions to adjust at least one of the following attributes, either singly or in any combination: a transmit pulse length, a transmit pulse amplitude envelope shape, a transmit pulse amplitude, a center frequency of a transmitted pulse, a spectral bandwidth of a transmitted pulse and an aperture width produced by said ultrasound transducer.

9. The method as recited in claim 1, wherein step (c) further adjusts power applied by said ultrasound beams to maximize a harmonic response from imaged tissue.

10. The method as recited in claim 9, wherein, prior to step (c), a contrast agent is administered to a patient whose anatomical construct is imaged in step (a) and step (c) adjusts said power to further maximize harmonic response from said contrast agent.

11. The method as recited in claim 2, wherein controlling step (c) controls said ultrasound transducer to produce plural transmit events along a subset of scan lines wherein said plural indications manifest plural foci along said subset of scan lines, said transmit events controlled so that said plural beams produced thereby respectively manifest the focus at each respective one of said plural focal points.

12. A memory media for controlling an ultrasound system to produce a desired locus of maximum power regions of plural transmit lines of an ultrasound scan, said memory media comprising:

a) means for controlling said ultrasound system to produce a display of an imaged region;

b) means for controlling said ultrasound system to superimpose on said display of said region, indications of a desired locus of maximum power regions of said plural transmit lines of said ultrasound scan; and c) means for controlling said ultrasound system to control an ultrasound transducer to produce ultrasound beams that scan said region, and to adjust said beams so that maximum power regions thereof occur, during said ultrasound scan, in accord with said indications.

13. The memory media as recited in claim 12, wherein means c) controls said ultrasound system to produce each said maximum power region of a beam by adjusting a focal point thereof.

14. The memory media as recited in claim 12, wherein said indications are configured as a graphical image on said display.

15. The memory media as recited in claim 12, wherein means (b) controls said ultrasound system to enable a user to superimpose said indications on said display and further enables said user to adjust said indications so as to revise their position on said display in relation to an anatomical construct imaged on said display.

16. The memory media as recited in claim 13, wherein said means (c) controls said ultrasound system to map said indications to respective closest allowed focal points, which allowed focal points are in turn used to control said focus of said ultrasound beam.

17. The memory media as recited in claim 13, wherein each said ultrasound scan comprises N transmit events of an ultrasound beam, plural ones of said transmit events controlled to manifest foci in accord with said closest allowed focal points.

18. The memory media as recited in claim 13, wherein the locus of foci is adjusted by means (c) controlling said ultrasound system to adjust coefficients used to control a transmit beam former forming a portion of said ultrasound system.

19. The memory media as recited in claim 12, wherein said means (c) controls said ultrasound system to employ data derived from selected loci of maximum power regions to adjust at least one of the following attributes, either singly or in any combination: a transmit pulse length, a transmit pulse amplitude envelope shape, a transmit pulse amplitude, a center frequency of a transmitted pulse, a spectral bandwidth of a transmitted pulse and an aperture width produced by said ultrasound transducer.

20. The memory media as recited in claim 12, wherein means (c) controls said ultrasound system to further adjust power applied by said ultrasound beams along said desired locus of maximum power regions to maximize a harmonic response from imaged tissue.

21. The memory media as recited in claim 20, wherein, a contrast agent is administered to a patient whose anatomical construct is imaged under control of means (a) and means (c) controls said ultrasound system to adjust said power to further maximize harmonic response from said contrast agent.

22. The memory media as recited in claim 13, wherein means (c) controls said ultrasound system to operate said ultrasound transducer to produce plural transmit events along a subset of scan lines wherein said plural indications manifest plural foci along said subset of scan lines, said transmit events controlled so that said plural beams produced thereby respectively manifest the focus at each respective one of said plural focal points.

* * * * *